(12) United States Patent
Thorpe et al.

(10) Patent No.: US 11,911,308 B2
(45) Date of Patent: Feb. 27, 2024

(54) RESTRAINT FOR SECURING A PERSON TO AN OBJECT, AND A CUT-RESISTANT WEBBING

(71) Applicant: The Crown in right of the State of New South Wales acting through the Department of Justice Corrective Services NSW, Corrective Services Industries, Sydney (AU)

(72) Inventors: Stephen John Thorpe, Sydney (AU); Kevin Desmond Corcoran, Sydney (AU); Derek Brindle, Sydney (AU); George Semertzidis, Victoria (AU)

(73) Assignee: The Crown in right of the State of New South Wales acting through the Department of Justice Corrective Services NSW, Corrective Services Industries, Sydney (AU)

( * ) Notice: Subject to any disclaimer, the term of this patent is extended or adjusted under 35 U.S.C. 154(b) by 1410 days.

(21) Appl. No.: 16/325,794

(22) PCT Filed: Aug. 17, 2017

(86) PCT No.: PCT/AU2017/050878
§ 371 (c)(1),
(2) Date: Feb. 15, 2019

(87) PCT Pub. No.: WO2018/032056
PCT Pub. Date: Feb. 22, 2018

(65) Prior Publication Data
US 2021/0378856 A1    Dec. 9, 2021

(30) Foreign Application Priority Data

Aug. 17, 2016 (AU) .................. 2016903260

(51) Int. Cl.
*A61F 5/37*        (2006.01)
*E05B 75/00*     (2006.01)

(52) U.S. Cl.
CPC .......... *A61F 5/3723* (2013.01); *A61F 5/3761* (2013.01); *E05B 75/00* (2013.01)

(58) Field of Classification Search
CPC ........ A61F 5/3723; A61F 5/3761; A61F 5/37; A61F 5/3769; A61F 5/3776; E05B 75/00; E05B 67/003
See application file for complete search history.

(56) References Cited

U.S. PATENT DOCUMENTS 539,650 A * 5/1895 Searle
7,000,438 B1  2/2006 Cooper et al.
(Continued)

FOREIGN PATENT DOCUMENTS

AU      2014202347      11/2014

*Primary Examiner* — Victoria Hicks Fisher
(74) *Attorney, Agent, or Firm* — Joel Skinner; Skinner and Associates

(57) ABSTRACT

A non-injurious restraint for securing a person to an object comprising a flexible strap comprised of, or including a substantially cut-resistant webbing associated with a strip of steel interlinked rings and reinforcement cables. A locking mechanism including one or more projections or pins adapted to engage the interlinked rings in forming a fixed length loop. The strap adapted to be secured to the object with the loop adjusted to encircle the limb, and wherein the locking mechanism locks the length of the loop. A webbing for use in such restraints.

4 Claims, 11 Drawing Sheets

(56) References Cited

U.S. PATENT DOCUMENTS

| | | |
|---|---|---|
| 7,121,122 B2 | 10/2006 | Levi |
| 2006/0243004 A1 | 11/2006 | Johnson et al. |
| 2010/0229350 A1* | 9/2010 | Kostal .................... E05B 75/00 24/16 PB |
| 2012/0321409 A1 | 12/2012 | Lesley |

* cited by examiner

RESTRAINT FOR SECURING A PERSON TO AN OBJECT, AND A CUT-RESISTANT WEBBING

TECHNICAL FIELD

The present invention relates to restraints for securing a limb of a person to an object, and a cut-resistant webbing suitable for use as a component of such restraints. In particular, the invention concerns a restraint with webbing including, comprising of, or incorporating a strip of reinforced interlinked rings which cooperates with a locking mechanism having a plurality of projecting pins adapted to engage the strip to form a fixed length loop to secure the limb to the object. Specifically, the invention is directed to a secure but non-injurious restraint over that of the prior art.

BACKGROUND TO THE INVENTION

Restraints for persons are often required by police, military, in courtrooms, in adult and juvenile corrective facilities, including extremism areas, in immigration centres, in treatment facilities for forensic patients and in mental healthcare facilities in order to restrict the movement of a person. For example, when a person is taken into custody by police, it is common for handcuffs to be secured by a police officer about the person's wrists in order to restrict movement of the person, and therefore protect the police officer and/or the person from harm being inflicted by the person. Similarly, handcuffs may be used to secure the person to another object, such as a vehicle, to prevent the person from escaping custody.

Handcuffs are a popular restraint device as they are relatively strong, secure and convenient to operate. A pair of handcuffs typically comprises a pair of openable metal cuffs secured to each other by a length of metal chain. Each cuff is dimensioned to receive a wrist/ankle and includes a ratchet mechanism to allow the cuff to be adjusted in size to snugly fit around the wrist/ankle, and be secured thereabout.

Whilst handcuffs are often suitable for restraining a person, there are many scenarios where handcuffs are inappropriate and potentially dangerous. For example, when a prison inmate who is known to be violent requires surgery, it is typical to secure the inmate's wrists and ankles to a hospital bed during surgery, and throughout recovery, to protect hospital staff from the inmate. This is not only uncomfortable for the inmate but can cause injury due to repetitive and/or forceful movement of the inmate's limbs. Similarly, if the same inmate was allowed out of prison to visit a dying relative in hospital, he/she would be required to wear one or more pairs of handcuffs due to the potential for a violent incident. However, this is often intimidating for hospital staff and other visitors at the hospital, and can therefore affect the quality of care being provided to the dying relative. In both of these scenarios, this also creates an opportunity for the inmate to escape custody, as a hospital environment is significantly less secure than a prison. This has resulted in escape attempts, whereby an inmate, or others assisting the inmate, cut through or otherwise disable the handcuffs, thereby allowing the inmate to flee.

Accordingly, it would be advantageous to provide a restraint for securing a limb of a person to an object, including another limb, which is more comfortable and/or safer for the person than prior art approaches, and/or which is more secure than prior art approaches.

Restraints are also often employed more generally to secure an object to a fixed location. For example, it is commonplace to secure cargo to a vehicle during transit, such as using 'tie-down' straps to retain the object to a roof rack. However, particularly where the cargo is valuable, such as a kayak or bicycle, it is known for such objects to be stolen due to the straps being cut or otherwise destroyed, and therefore allowing the equipment to be removed from the roof rack.

Accordingly, it would also be useful to provide a cut-resistant strap for securing an object to a fixed location which is less prone to destruction than prior art approaches.

Furthermore, it would be useful to provide a solution to any of the problems discussed above that avoids or ameliorates any of the disadvantages present in the prior art, or which provides an alternative to prior art approaches.

SUMMARY OF THE INVENTION

According to one aspect of the invention there is provided a restraint for securing a limb of a person to an object, the restraint comprising a flexible strap defined by opposed ends and opposed edges and comprising between the ends, a substantially cut-resistant webbing incorporating a strip of interlinked rings; and at least one locking mechanism including one or more projections or pins adapted to engage the interlinked rings thereby forming the strap into a fixed length loop, and disengage therefrom responsive to operation with a key, in use, the strap is adapted to be secured to the object and the loop adjusted to encircle the limb, and wherein the at least one locking mechanism engages the webbing thereby fixing the loop length and securing the limb to the object.

In another aspect, the present invention relates to a cut-resistant webbing able to be used in a restraint; the webbing defined by opposed ends and opposed edges including a strip of interlinked rings extending at least partially between the ends.

Preferably, the interlinked rings are arranged in a grid-like array.

In one example, each of the interlinked rings is interlinked with at least two other rings.

In another example, at least some of the interlinked rings are interlinked with four other rings.

Preferably, each of the interlinked rings is circular.

Preferably, each of the interlinked rings is formed from an inert metal and is encased in resin.

In a preferred embodiment of the restraint, the at least one locking mechanism comprises one or more pins having complementary shaped ends adapted to move in the direction of and to engage with one or more interlinked rings in the webbing.

Preferably, the locking mechanism is configured to self-lock responsive to the one or more pins moving beyond a defined threshold position.

Preferably, the locking mechanism further comprises a slot dimensioned to receive the strap, and the one or more pins are arranged to urge against a portion of webbing passing through the slot to engage the webbing. The one or more pins are preferably arranged to move across the slot. The slot also defines a direction along which a portion of webbing is passed, and each of the plurality of pins have a free end arranged to abut the portion of webbing in the slot, with at least some of the free ends being curved in a direction perpendicular to the direction of the slot. At least some of the pins are arranged to urge against the webbing.

The interlinked rings define a respective plurality of apertures, and the free ends of some of the pins are preferably curved and dimensioned to at least partially fit within the apertures. More preferably, each of the plurality of pins are dimensioned to fit wholly within the apertures.

Preferably, at least one locking mechanism is attached to an end of the strap and is releasably attached to that end.

In a preferred example, the respective end further comprises a termination assembly, and the locking mechanism defines an aperture mechanism for engaging the termination assembly.

In an alternative example, the disengagement of the projections or pins of the locking mechanism, from the interlinked rings, is responsive to operation with a digital key.

The restraint further comprises a pair of reinforcement cables connected to the webbing forming part of the selvedges of the webbing.

Preferably, the webbing is located between the cables. Preferably each of the cables is formed from metal and encased in resin. More preferably, each of the cables is wire rope.

In a preferred embodiment, the strap is comprised entirely of the webbing and a pair of cables. The strap can be tubular and can define tubular portions respectively dimensioned to enclose a strip of interlinked rings and the cables.

Preferably, the webbing has a warp and weft comprising aramid fibres.

More preferably, the warp further includes polyester fibres.

Preferably, the aramid is PPTH.

Other aspects and various embodiments are disclosed.

BRIEF DESCRIPTION OF THE DRAWINGS

Preferred embodiments of the invention will now be described, by way of example only, with reference to the accompanying drawings in which.

DETAILED DESCRIPTION OF PREFERRED EMBODIMENTS

Figure 1:
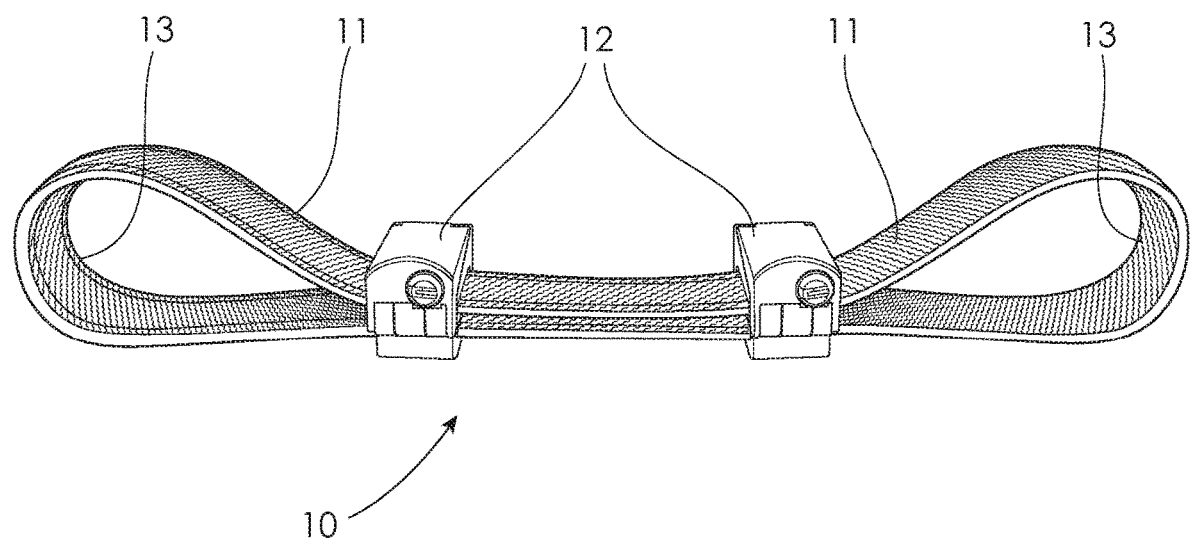
FIG. 1 is a perspective view of a preferred restraint according to the invention.

The present disclosure relates generally to a restraint for securing a limb of a person to an object, which can include another limb of the same or another person, and a cut-resistant webbing for such restraints or for that matter, restraints for securing one object to another object which also forms part of the disclosure.

In particular, a restraint for securing a limb of a person to an object is disclosed. The restraint comprising a flexible strap, the strap defined by opposed ends and opposed edges and including, comprising or incorporating at least partially between the ends, a substantially cut-resistant webbing, itself comprising of, or enclosing a strip of interlinked rings; at least one locking mechanism having one or more projecting pins adapted to engage the rings in forming a fixed length loop, responsive to operation with a key; the strap adapted to be secured to the object with the loop adjusted to encircle the limb, wherein the locking mechanism locks the length of the loop in non-injuriously securing the limb to the object.

Also, a further restraint for securing a limb of a person to an object is disclosed which includes a flexible webbing defined by opposed ends and extending between opposed edges; the webbing connected to at least one reinforcement element, typically, a pair of high tensile steel cables, or a strip of interlinked rings, or both, extending at least partially between the ends; at least one locking mechanism secured to the webbing and arranged to engage the webbing to form a fixed length loop, and responsive to operation with a key.

Use of the restraints involves formation of a fixed length loop about the limb, and engaging at least one locking mechanism with the strap or webbing, thereby fixing and locking the loop length to secure the limb in a non-injurious manner to the object.

Also disclosed is a cut-resistant webbing able to be used in a restraint; the webbing defined by opposed ends and opposed edges and comprising of, or enclosing a strip of interlinked rings extending at least partially between the ends.

The construction of the restraints and the cut-resistant webbing has been found to be highly resistant to attack with a range of tools and cutting implements, and has been shown to be equivalent to or more secure than known comparable restraints, such as handcuffs. This is at least partly because the interlinked reinforcement ring structure is flexible, allowing the rings to move relative to each other making cutting difficult. Furthermore, the ring structure is inherently strong and therefore resistant to not only cutting but plastic deformation which would otherwise weaken the reinforcement strip. This is advantageous as it ensures a person or a possession secured to an object using the restraint or cut-resistant webbing is less likely to be able to respectively, escape custody or be stolen. This may be further enhanced by associating one or more cables with the reinforcement structure, particularly so when the cables are configured as wire ropes, as the cables further resist cutting. The cables are preferably formed from high tensile non-corrosive metal, such as galvanised or stainless steel.

The structure of the disclosed restraints is also beneficial as the strap is arranged so that only flexible webbing material contacts the limb of the restrained person. This significantly reduces or eliminates abrasions, lacerations or other harm caused to the person by the restraint when compared to known comparable restraints, such as handcuffs, particularly when the person needs to be restrained for an extended period of time, for example, a number of weeks after surgery. This may be further enhanced by the webbing being formed from a hypoallergenic material, thereby reducing potential allergic reactions caused by contact with the restraint.

At least one of the disclosed restraints comprises a locking mechanism releasably secured to the strap. This is advantageous as removal of the locking mechanism from the strap allows the material to be washed. This is particularly useful when the restraint is used in a medical environment, as this allows bodily fluids, such as blood, to be washed out of the webbing, and also to be disinfected to remove potentially harmful pathogens.

The locking mechanism of any of the restraints typically comprises one or more pins which are movable to firmly abut against the webbing, thereby engaging the locking mechanism with the webbing. Typically, the locking mechanism includes a slot dimensioned to receive the webbing and the pins are movable across the slot, thereby urging a portion of the webbing arranged in the slot against a side of the slot to also frictionally engage the locking mechanism with the webbing. The pins are also typically adapted to form a secure engagement with the interlinked ring reinforcement structure, for example, by having curved end portions dimensioned to at least partially fit within the rings and/or spaces between the rings. The pins generally do not penetrate through the webbing into the interlinked rings but instead form a strong frictional and positive engagement with the webbing via the strip of rings to clamp the webbing in the slot.

In use, when the pins are engaged with the interlinked ring reinforcement structure, the curved end portions of the pins may not initially engage or fit within the rings and/or spaces between the rings. However, because the pins are under a clamping force, and there is some movement of the restraint when securing a limb of a person, there is a natural tendency for the end of the pins to bed down through the flexible webbing in the rings and/or spaces between the rings.

Referring now to the drawings, FIG. 1 shows a preferred restraint 10 for securing a limb of a person to an object. The restraint 10 comprises an elongate length of flexible webbing forming a strap 11 to which at least one locking mechanism 12 is adapted to lock the strap 11 in a fixed length loop 13 to receive a limb of a person or an object. It is important that the loop 13 is fixed at a defined length when the locking mechanism 12 engages the strap 11. This is so the loop size cannot be varied to dangerously restrict blood circulation or allow the loop 13 to be removed from the limb.

In this example, the strap 11 is entirely formed from flexible webbing material comprising woven fibres. For example, the webbing may comprise a warp and weft of strong, abrasion-resistant fibres, such as para aramid and/or polyester fibres. The fibres are typically woven together in a herringbone pattern to produce a distinctive, highly visible surface pattern. Alternatively or additionally, coloured fibres may also be woven into the webbing material. In either case, this can be useful for indicating the intended purpose of the restraint 10. For example, a black and yellow herringbone pattern may indicate the restraint 10 is for use with a prison inmate during transit. Alternatively, a mint green and white pattern may indicate the restraint 10 is for use with a person being treated in a mental health facility.

The strap 11 is connected to at least one reinforcement structure (not shown in FIG. 1) to increase the strength and/or cut resistance of the strap 11. For example, the strap 11 may typically enclose a strip comprising a plurality of interlinked rings (not shown in FIG. 1) and one or more high tensile steel cables (not shown). The reinforcement structure extends at least partially along the length of the strap 11, and typically its entire length. Details of the reinforcement structure are described below and shown in FIGS. 9A to 9D.

As shown in FIG. 1, the restraint 10 may include a pair of locking mechanisms 12, which allow each end of the strap 11 to be secured in a fixed length loop 13. Each locking mechanism 12 is either permanently or releasably connected to a respective end of strap 11. The strap 11 is then arranged to form a loop 13 proximal to each end and engaged by the respective locking mechanism 12, in fixing the length of the loop.

In another embodiment, the restraint 10 may include a single locking mechanism 12, which allows one end of the strap 11 to be secured in a fixed length loop 13. The locking mechanism 12 is either permanently or releasably connected to the end of the strap 11. The strap 11 can be arranged to form a loop 13 proximal to the end and engaged by the locking mechanism, in fixing the length of the loop. In this embodiment, the single fixed length loop 13 encircles both the object and limb of the person, thereby securing the limb to the object.

Typically, engagement of the locking mechanism 12 with the strap automatically places the locking mechanism 12 in a locked position. This may involve moving a portion of the locking mechanism 12 past a predetermined threshold position, causing the mechanism 12 to automatically engage and lock the strap 11. This is an advantage wherein a key is not required to lock the strap 11. Each locking mechanism 12 may then be unlocked with a key (not shown). The key is typically a physical key (not shown) however may be configured as a 'digital key', for example, a suitably programmed RFID tag which causes an RFID reader within the locking mechanism 12 to unlock the mechanism. In this scenario, the locking mechanism 12 would typically be powered, for example, by a battery. Alternatively, the locking mechanism 12 may comprise a passive/battery assisted passive RFID tag which is interrogated by an RFID reader (the 'digital key') and responsive to the key receiving an authorised identification code, the key wirelessly communicating with the locking mechanism 12 to operate the mechanism and disengage the strap 11.

Figure 2A:
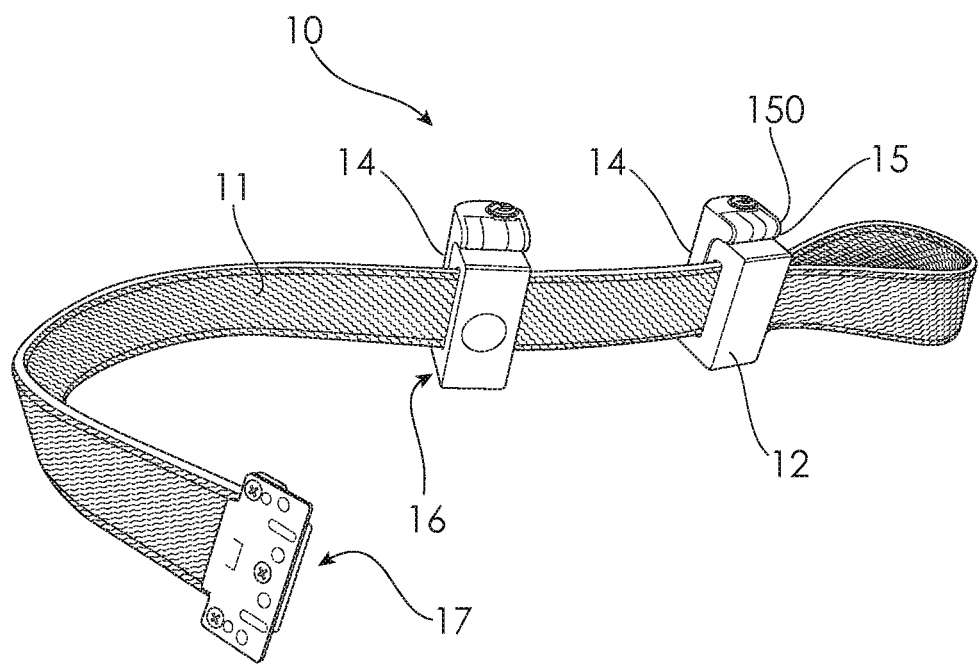
FIGS. 2A and 2B are perspective detailed views of two different configurations the restraint of FIG. 1.
Figure 2B:
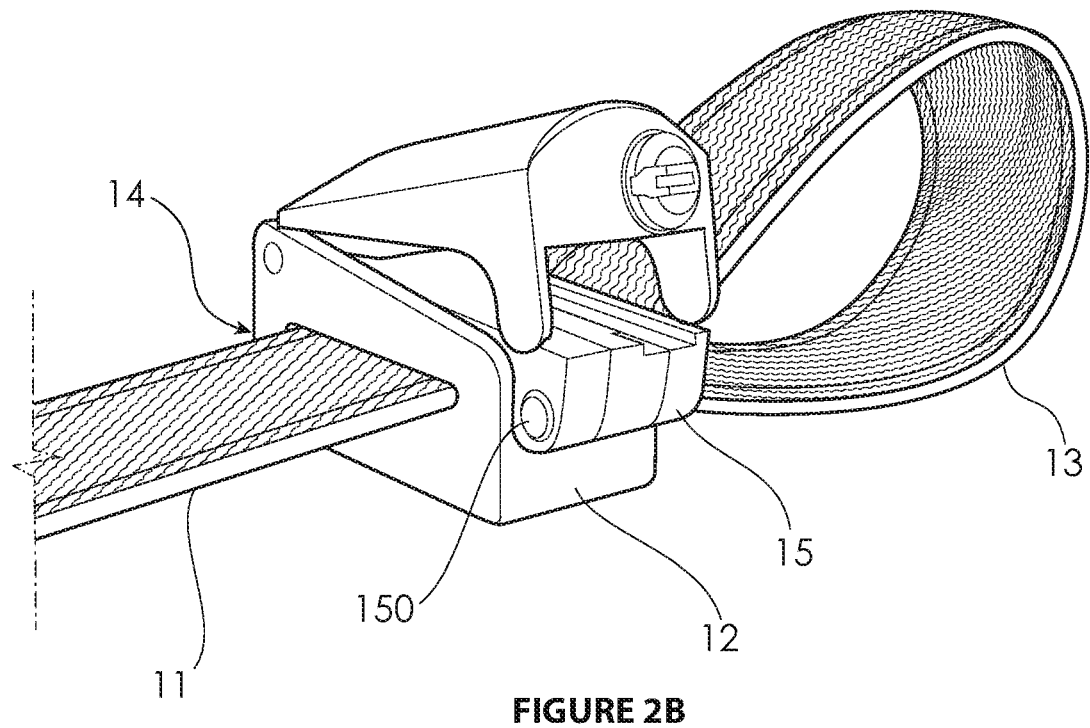

FIGS. 2A and 2B show detail views of the restraint 10, illustrating a preferred arrangement of the strap 11 relative to the locking mechanism 12. The locking mechanism 12 typically defines a slot 14 dimensioned to receive the strap 11, and an engagement mechanism (not shown) to enable engagement of the strap 11 in the slot 14. The slot 14 may comprise the sides of opposable jaws 15. Jaws 15 are pivotable with respect the body of the locking mechanism 12 about pivot 150 to allow the strap 11 to be positioned and locked in the slot 14. This configuration acts as the mechanism for engaging the locking mechanism 12 with the strap 11, and whereby pivoting the jaws 15 towards the body of the locking mechanism past a positional threshold, clamps the strap 11 and activates the locking mechanism 12. Each jaw 15 may include a surface finish or other features (not shown) to further increase friction to firmly engage the strap 11.

The locking mechanism 12 may further comprise an aperture 16 dimensioned to receive the termination assembly 17 secured to an end of the strap 11, as well as an engagement mechanism (not shown) for engaging the termination assembly 17. This allows the locking mechanism 12 to be releasably secured to the end of the strap 11, and enables removal of the locking mechanism 12 from the strap 11. Alternatively, if removal of the locking mechanism 12 from the strap 11 is not required, the locking mechanism 12 can be permanently secured to the end of the strap 11. For example, a portion of the locking mechanism 12 may be over-moulded, or otherwise integrally formed with the end of the strap 11, such that the locking mechanism 12 cannot be removed from the strap 11.

Figure 3:
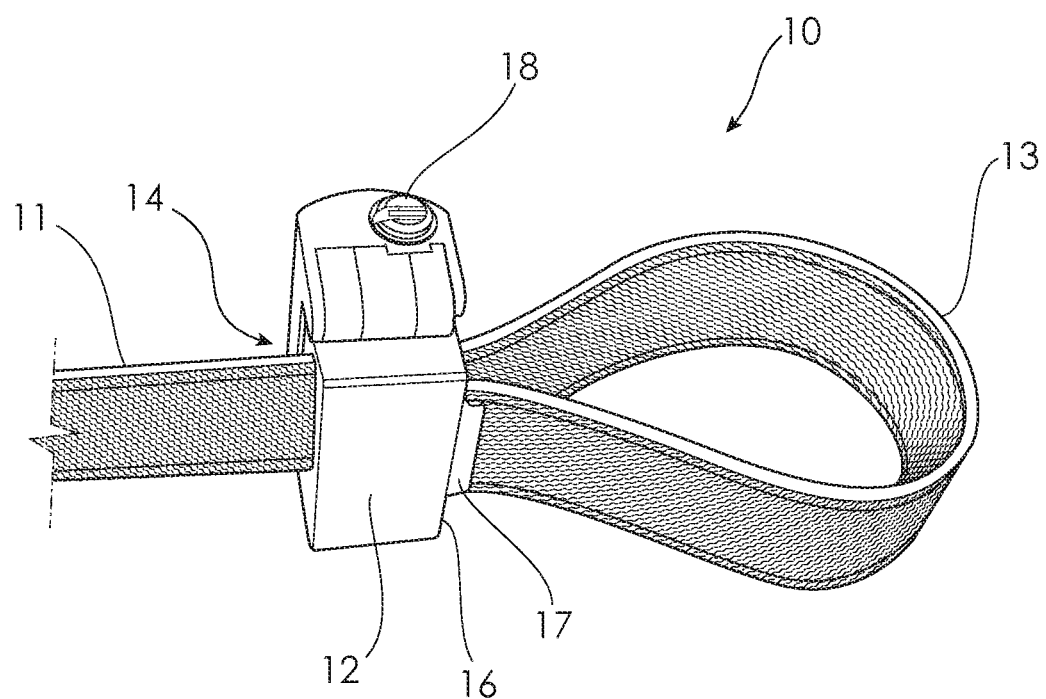
FIG. 3 is a perspective detailed view of the loop and locking mechanism.

FIG. 3 shows the restraint 10 with the strap 11 passing through slot 14 and locking mechanism 12 which is engaged with the strap to form loop 13 of a fixed length. Part of termination assembly 17 is shown retained in the aperture 16. A lock barrel 18 with a key hole dimensioned to receive a key (not shown) protrudes from one side of the locking mechanism 12. The lock barrel 18 typically houses an eight pin lock having a small diameter locking block to resist the lock barrel 18 being picked or otherwise tampered with to disengage the locking mechanism 12 from the strap 11.

Figure 4A:
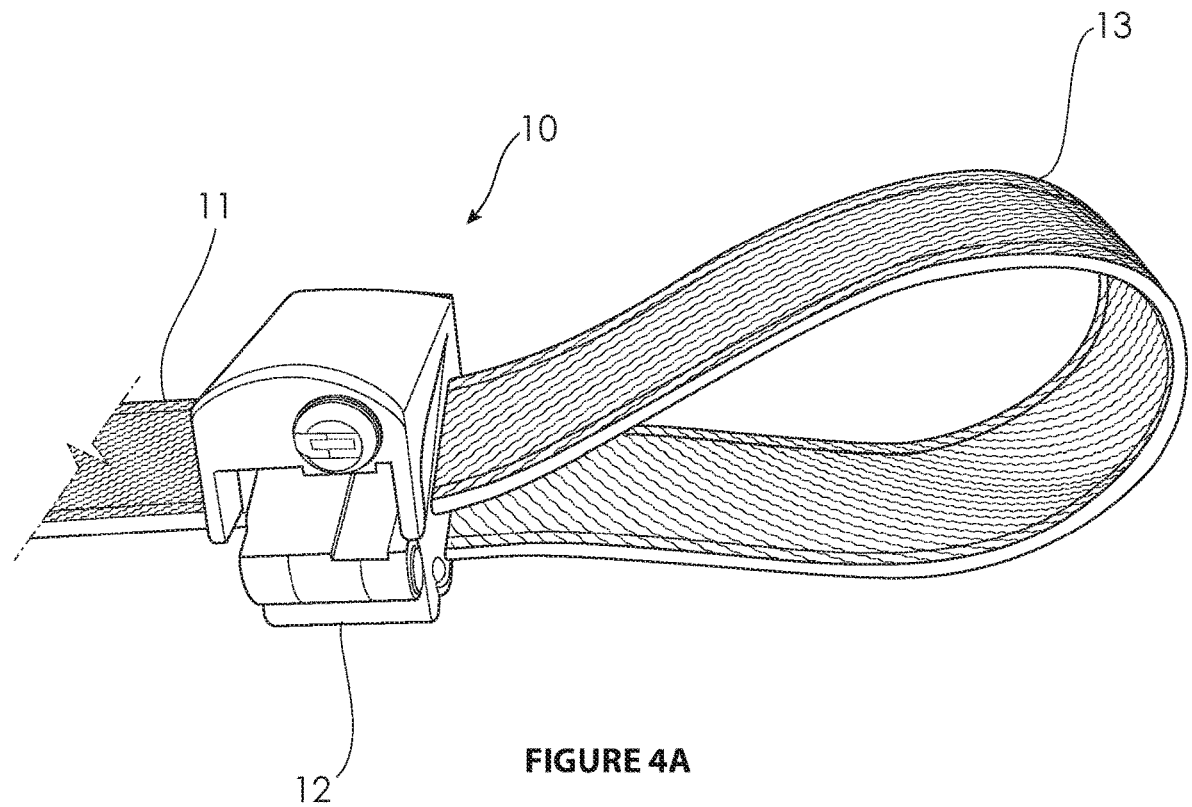
FIGS. 4A and 4B are perspective detailed views of the restraint shown in the previous drawings in two stages of adjustment.
Figure 4B:
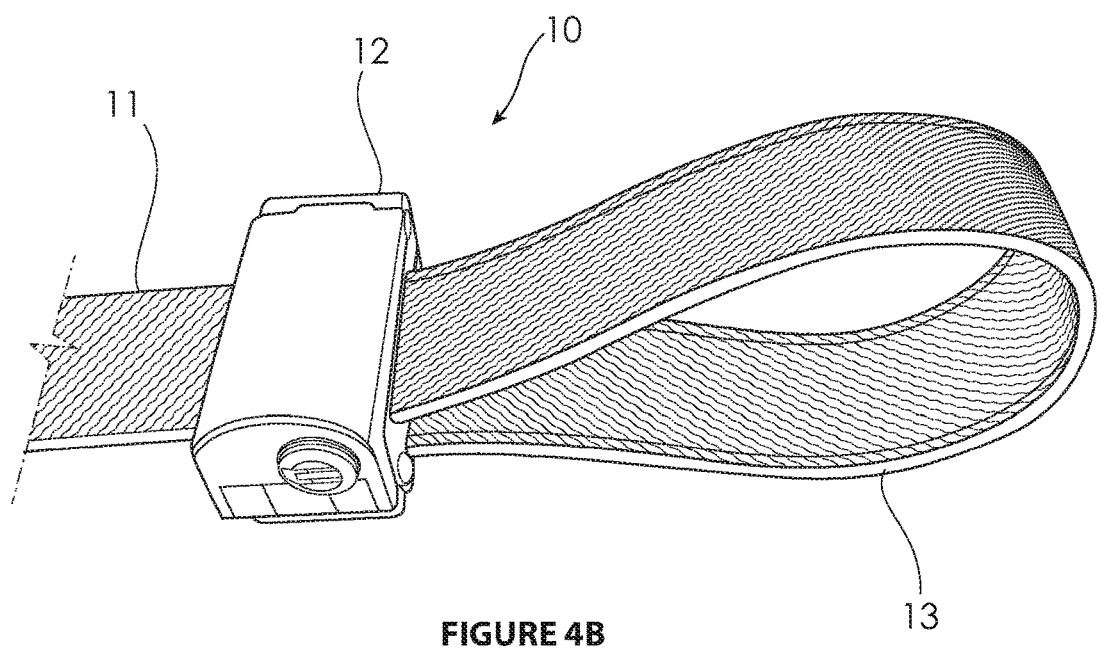

FIGS. 4A and 4B show two stages of use of the restraint 10. In FIG. 4A, the strap 11 is arranged in the slot 14 and the locking mechanism 12 is not engaged with the strap 11. This allows the length of the loop 13 to be adjusted, for example, around a limb or object to provide a secure fitment. In FIG. 4A a long loop 13 is shown and in FIG. 4B a short loop is shown. In FIG. 4B, the locking mechanism 12 is engaged with the strap 11, securing the loop 13 at a fixed length.

Figure 5:
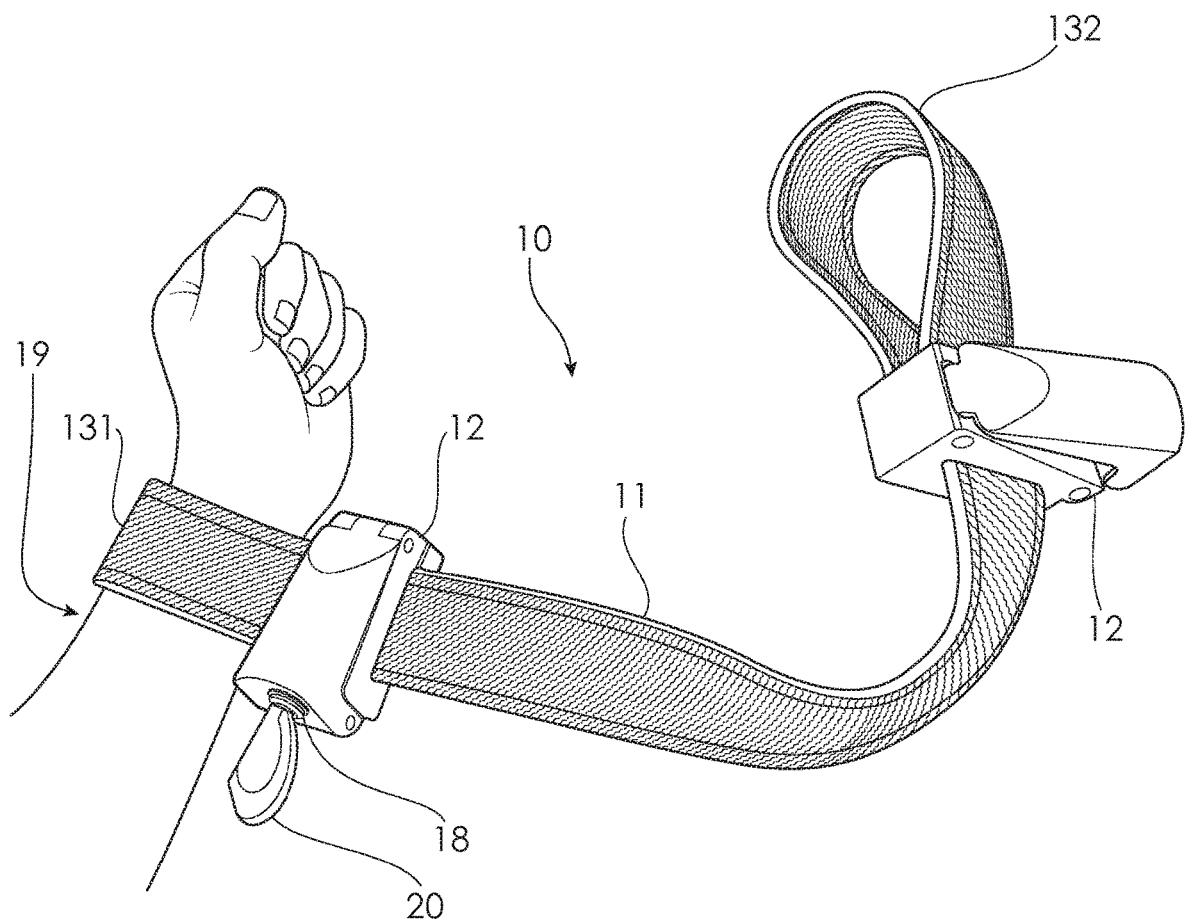
FIG. 5 is a perspective view of the restraint shown in the previous drawings secured about a wrist of a person.

FIG. 5 shows the restraint 10 in use. The strap 11 has been arranged to form a pair of loops 13 at each end engaged by respective locking mechanisms 12. A limb 19 of a person is encircled and restrained by a first loop 131 and a second loop 132 may be secured to an object (not shown), such as a hospital bed, or another limb (not shown).

The lock barrel 18 can be described as two locks in one, with dual-bladed keys being cut on two independent rows of pin tumblers, wherein each row of pins activate a separate side bar. This arrangement significantly resists or prevents picking. In addition, the pins are especially shaped and 'blunted' to frustrate attempts at impressioning. Each cylinder can also be fitted with optional hardened steel pins to resist drilling.

A key 20 is shown positioned in the lock barrel 18 in FIG. 5. Rotating key 20 disengages the locking mechanism 12 from the strap 11. The key 20 is typically a dual bladed key, having a U-shaped profiled portion for engaging lock barrel 18 to further enhance tamper-resistance of the lock barrel 18. Each blade of the dual bladed key is cut to a different combination before forming the distinctive 'U' shape. Effectively, this results in there being two different keys operating simultaneously in one lock barrel 18, making it very difficult for any unauthorised opening of the lock.

It is not shown in the drawings, but a different key can be inserted into the lock barrel 18, which serves not only to disengage the load pins from the strap 11, but can also allow the lock barrel to be removed from the locking mechanism, for example in the case of a fault in the lock barrel. This other key when operated in a different way can also be used to 'open' the locking mechanism completely so that the locking mechanism can be removed from the strap 11. For example, this would be done when it was desirable to wash the strap 11 of the restraint 10.

Figure 6:
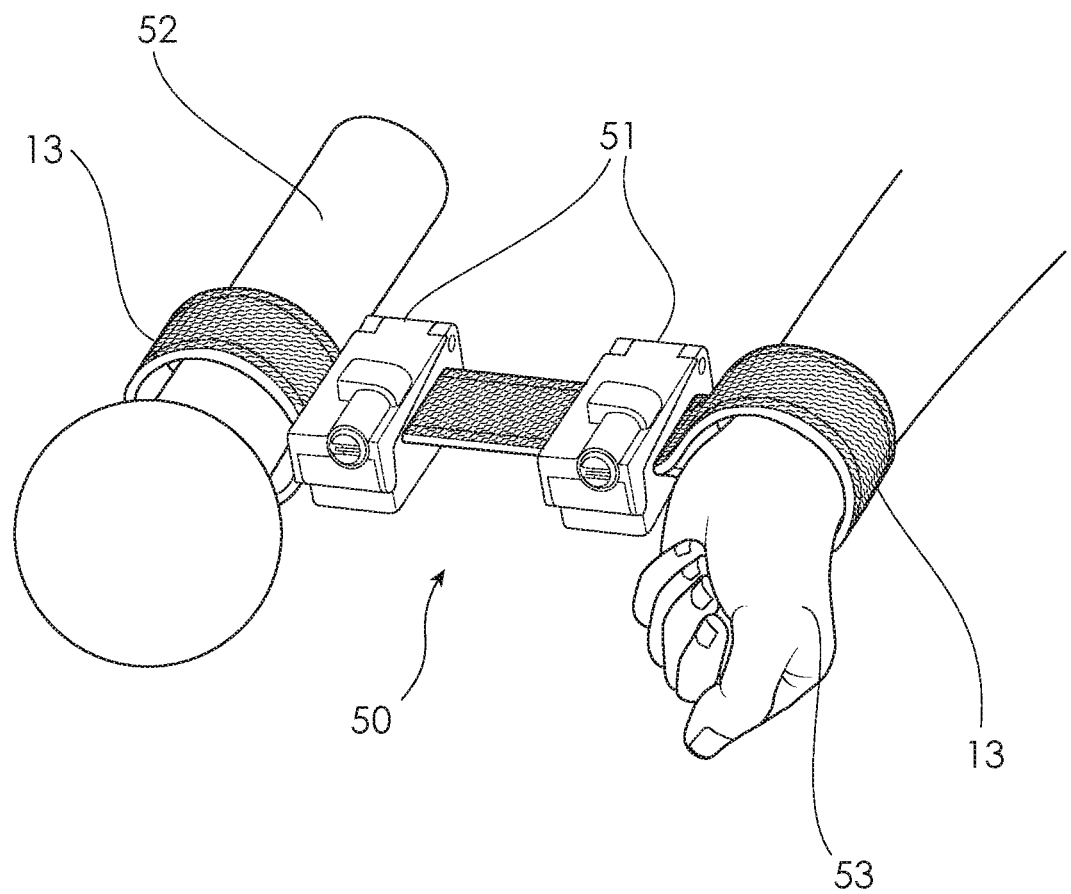
FIG. 6 is a perspective view of an alternative restraint secured between two objects.

FIG. 6 shows an alternative restraint 50 sharing some of the features of the restraint 10 previously described. The same reference numerals are used to indicate common features. The restraint 50 includes the strap 11 and at least one alternative locking mechanism 51 for engaging the strap 11 to form loops 13 of fixed lengths. The restraint 50 is shown having two locking mechanisms 51 engaged with the strap 11 forming two fixed length loops 13, one loop secured about pole 52, the other loop securing limb 53.

Figure 7A:
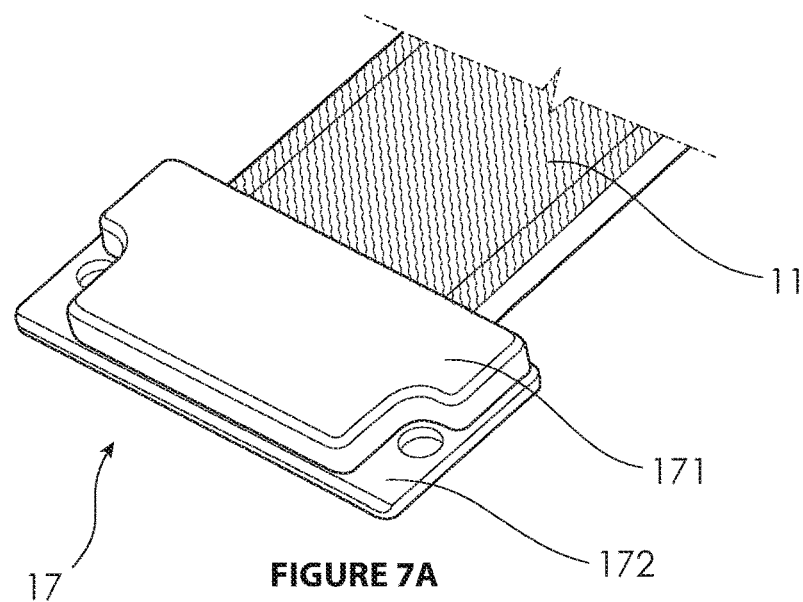
FIGS. 7A and 7B are a perspective detail view and an exploded detail view respectively of a sub-assembly of the restraint shown in FIG. 6, being a termination assembly.
Figure 7B:
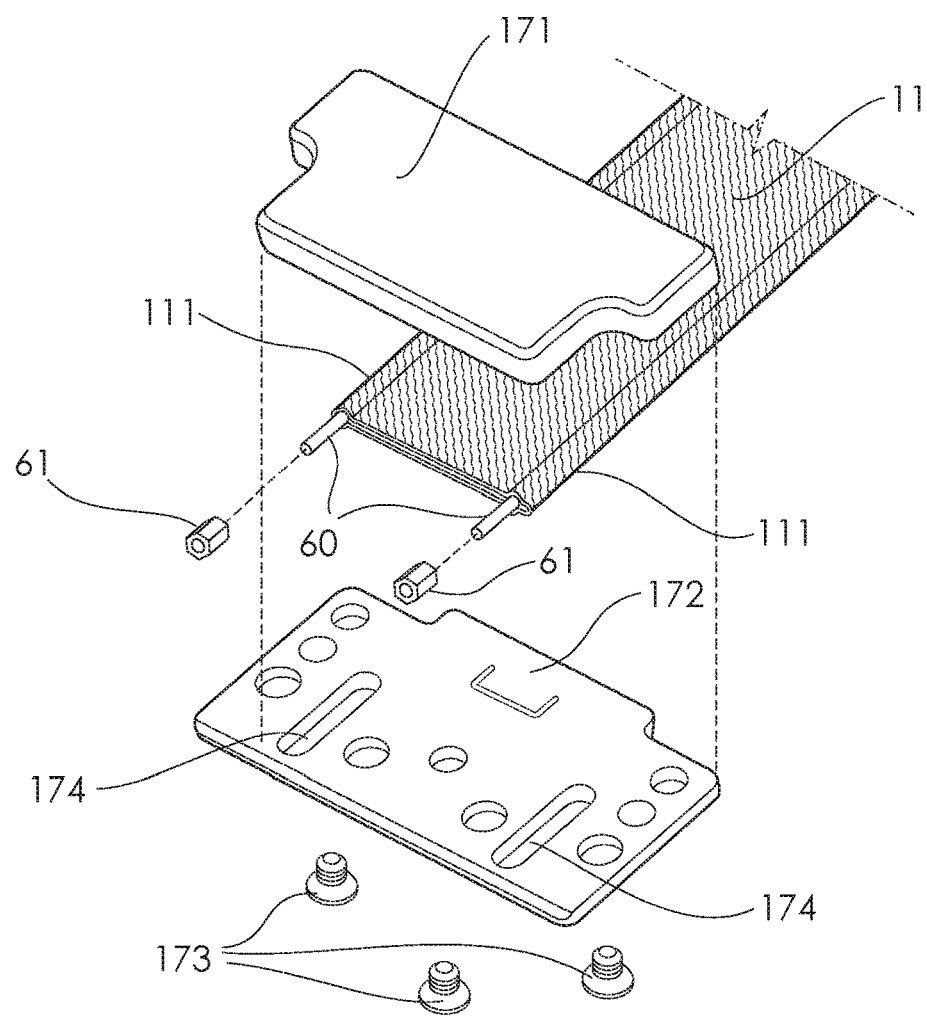

FIGS. 7A and 7B show the termination assembly 17 in further detail. The termination assembly 17 comprises a top plate 171, bottom plate 172 and fasteners, configured as rivets 173, for securing the plates 171, 172 together. The plates 171, 172 are arranged on either side of the strap 11 and are joined together to permanently secure the termination assembly 17 to the strap 11. Typically, the strap 11 encloses a pair of cables 60 arranged along opposed edges 111 thereof. The cables 60 typically extend between each end of the strap 11 and are secured between the plates 171, 172. Engagement of the cables 60 to the plates may be facilitated by fixing an end of each cable 60 to a sleeve 61 dimensioned to be received in a recess or an aperture 174 in one or more of the plates 171, 172.

Figure 8A:
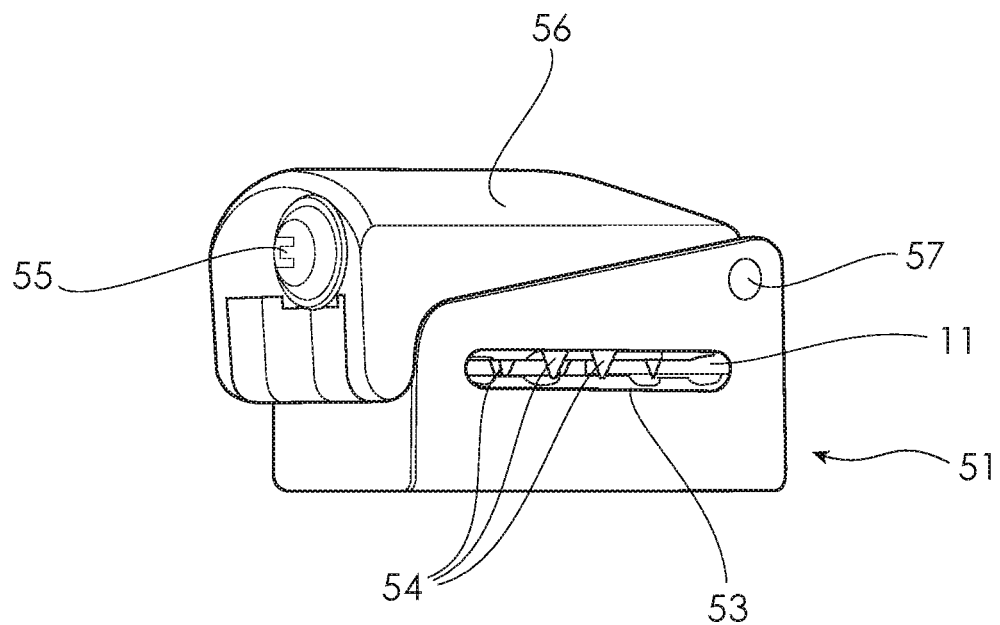
FIGS. 8A and 8B are perspective and front views of another sub-assembly of the restraint shown in FIG. 6, being a locking mechanism assembly.
Figure 8B:
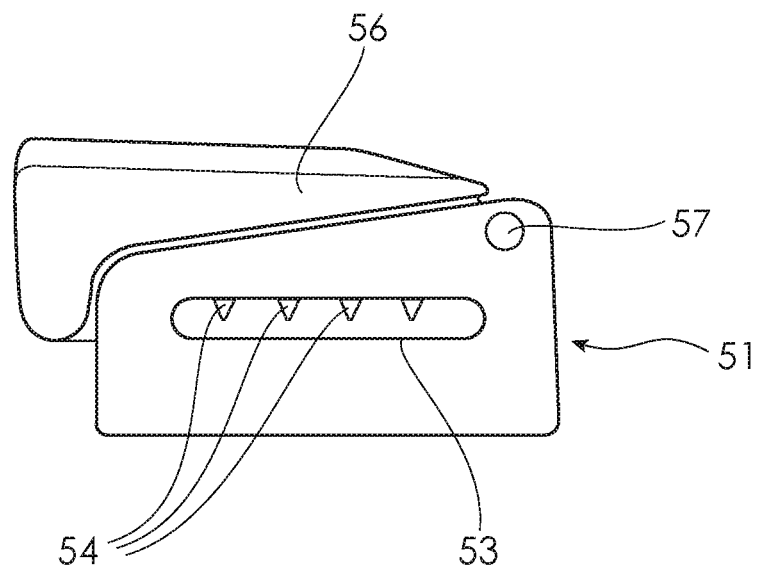

FIGS. 8A and 8B show the locking mechanism 51 in isolation. The locking mechanism 51 defines a slot 53 dimensioned to receive at least a thickness of the strap 11. Proximally to the slot 53 are one or more pins 54 which are selectively movable at least partially across the slot 53 to engage the strap 11. Operation of the locking mechanism 51 to engage the strap 11 moves the pins 54 across the slot 53, typically until the pins 54 pass a defined threshold position causing the locking mechanism 12 to automatically lock itself.

The locking mechanism 51 typically includes a pivotable portion 56 which pivots about an axis 57. Pivoting the pivotable portion 56 to a defined position automatically operates the locking mechanism 51 which moves the pins 54 across the slot 53 to engage the strap. The mechanism 51 also houses a lock barrel 55 which may be operated by a key (not shown) to disengage the pins 54 from the strap 11.

Figure 8C:
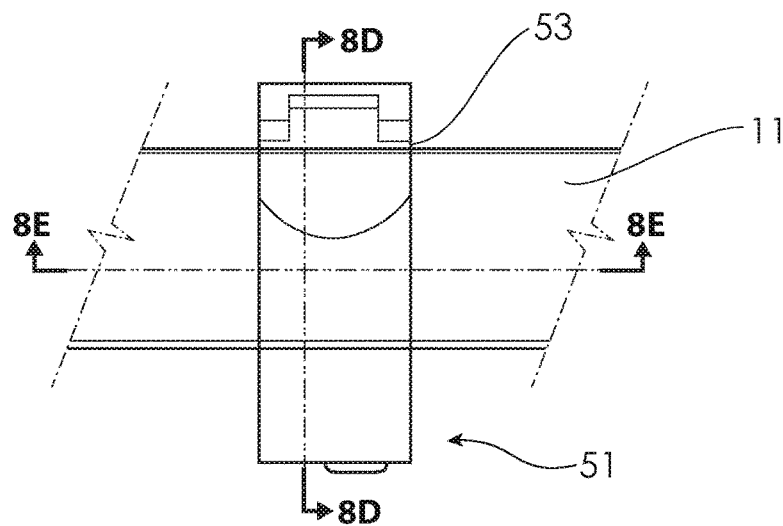
FIGS. 8C to 8E are top and cross-sectional views of a variation of the locking mechanism assembly shown in FIGS. 8A and 8B.
Figure 8D:
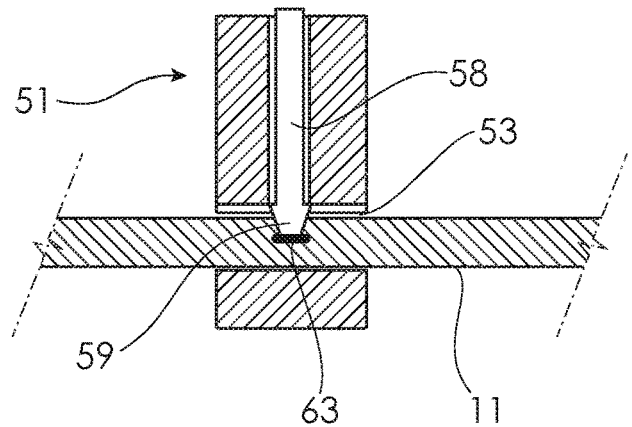
Figure 8E:
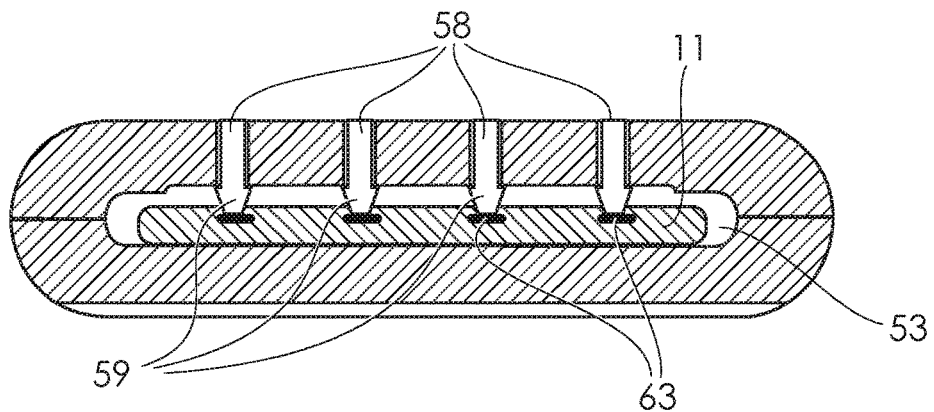

FIGS. 8C to 8E show various sections of the locking mechanism 51 wherein the same reference numerals are also used to indicate common features.

FIG. 8C shows a top view of the locking mechanism 51 with strap 11 passing through the slot 53 and the locking mechanism 51 engaged with the strap. Slot 53 defines a longitudinal direction along which strap 11 passes through the locking mechanism 51. FIG. 8C also illustrates two cross-sections: E-E and D-D.

FIG. 8D shows the restraint 50 from cross-sectional plane, E-E illustrating an alternative pin 54 configured as a post 58. The locking mechanism 51 comprises a plurality of posts 58 arranged proximal to the slot 53 and movable across the slot 53, thereby being arranged to abut and urge against strap 11 passing through slot 53. The locking mechanism 51 is configured to exert substantial force through the posts 58 to frictionally engage and clamp the strap 11 in the slot 53, preventing its removal therefrom. The posts 58 typically have free ends 59 for abutting the strap. The free ends 59 are typically shaped to form a right angle with a side of the post 58, thereby enhancing frictional engagement with the strap 11. Alternatively, the free end 59 may have a sharpened or bevelled point, to further increase friction between the post 58 and strap and to positively engage with interlinked rings 63 in the webbing material of the strap. In the embodiment shown in FIGS. 8C to 8E, the posts 58 are typically designed not to penetrate the strap 11. This feature is in the interest of not degrading, by repeated use, the webbing material and/or the metal reinforcement structures, which may decrease the useful life of the strap 11.

FIG. 8E shows the restraint 50 from cross-sectional plane, D-D showing the posts 58 urged against the strap 11. The free ends 59 of posts 58 are shaped to have a rounded surface with a curved profile. The curved profile enhances engagement with the interlinked rings 63, as the free ends 59 may be dimensioned to at least partially penetrate or otherwise engage the rings or apertures between adjacent rings. Typically, the curved profile is perpendicular to the direction along which the strap 11 passes as defined by the slot 53 to enhance this effect.

Figure 9A:
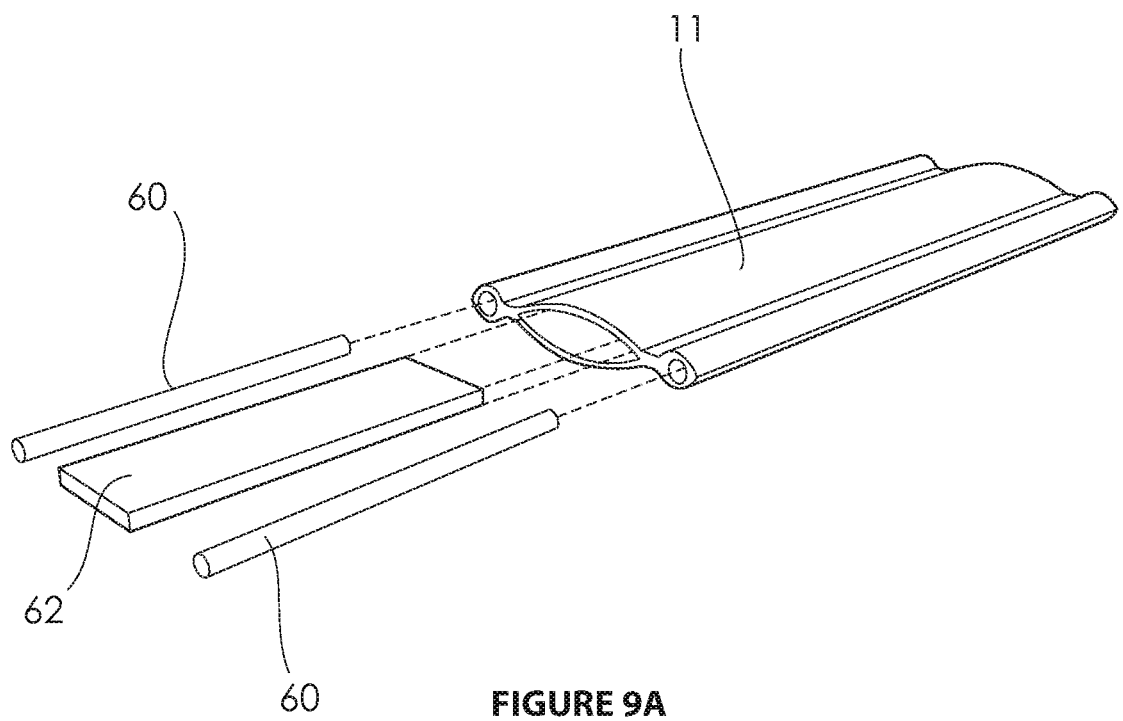
FIGS. 9A and 9B are exploded and cross-sectional views of a webbing suitable for use in the restraints shown in the previous drawings.
Figure 9B:
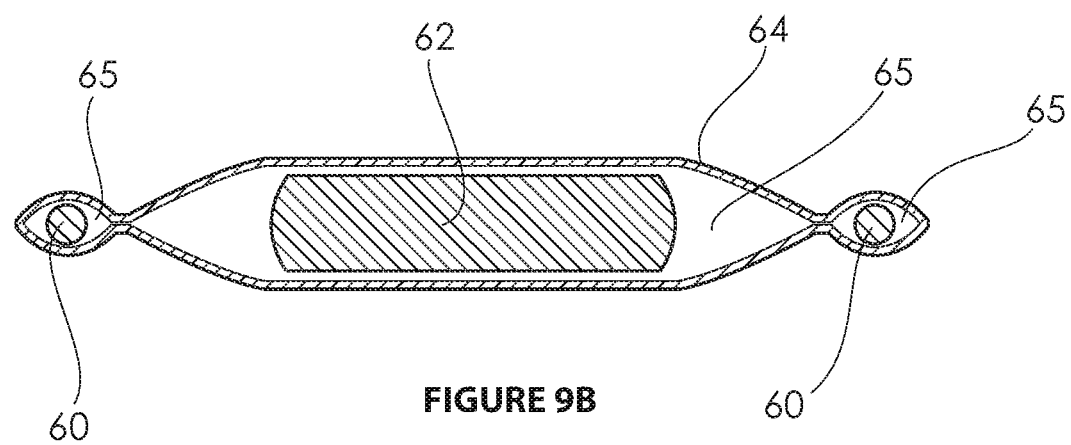
Figure 9C:
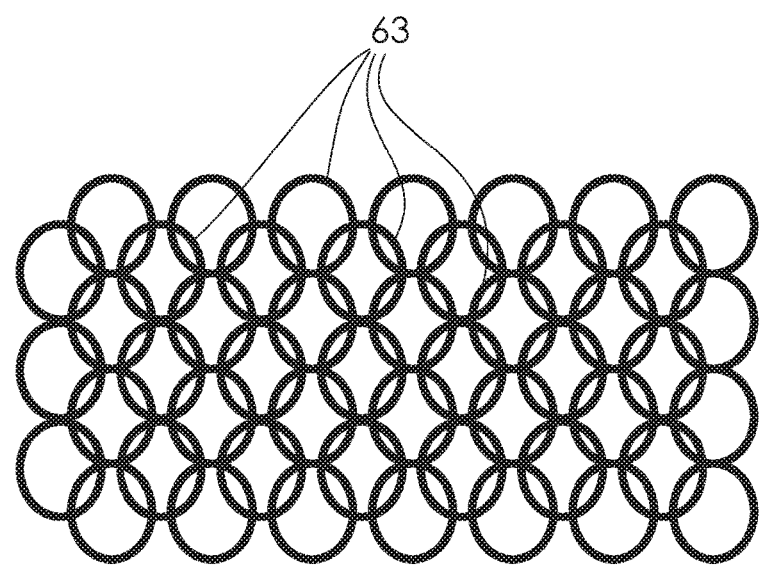
FIG. 9C is a top view of another sub-assembly of the restraint shown in FIG. 6, being a strip of interlinked rings.

FIGS. 9A to 9D illustrate the construction of strap 11 in more detail. It will be appreciated that the strap 11 may be used alone, for example, to tie a valuable possession to a fixed location to prevent its theft. The strap 11 is connected to at least one reinforcement element which extends at least partially between opposed ends of the strap 11. The reinforcement element is configured as a strip 62 formed from a plurality of interlinked rings 63, as best shown in FIG. 9C. The strap 11 has two further reinforcement elements, namely cables 60, arranged along opposite edges of the strap 11.

Best shown in FIG. 9B, the strap 11 is formed from a tubular webbing 64 which defines three tubular portions 65 for receiving and enclosing the strip 62 and opposed cables 60. The strip 62 and cables 60 are typically of metal, such as stainless steel, and are encased in resin, such as a plastisol. The metal has strong cut-resistant properties, whilst the resin coating is useful to reduce or eliminate corrosion of the metal, such as through oxidation, and also enhances flexibility of the reinforcement elements, For example, the resin coating on the rings 63 reduces friction between rings 63 which allows rings 63 to move relative to each other. The resin coating on the rings 63 also assists in preventing the rings from collapsing, whereby the strip 62 is able to maintain its shape. The cables 60 are typically configured as multi-strand wound cables. Typically they are 'wire ropes' (not shown), comprising a plurality of strands, each formed from a plurality of wires, wound around a core. The wire rope configuration optimises cut resistance, as the strands move relative to each other. This makes them somewhat compressible which also makes them difficult to sever.

Best shown in FIG. 9C, the strip 62 typically comprises a plurality of interlinked circular rings arranged in a grid-like array. This involves each ring 63 interconnecting at least two other rings 63, with the majority of rings interconnecting four other rings 63, thereby forming a very strong lattice-like structure. Whilst the rings 63 are shown as circular rings, it will be appreciated that the rings 63 may have other configurations, such as having a hexagonal shape. Alternatively, the rings 63 may be configured as a lattice of interconnecting plates (not shown).

Figure 9D:
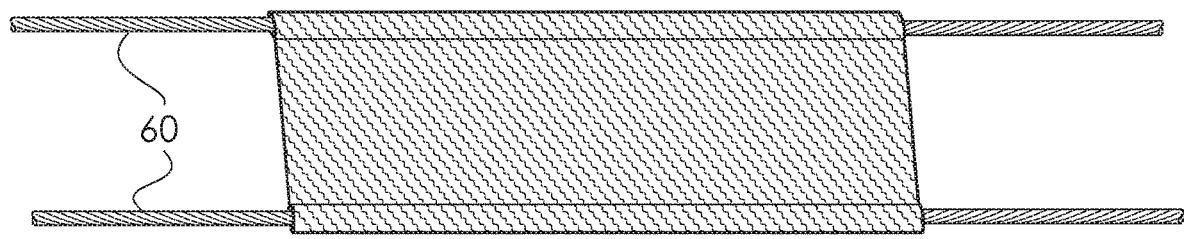
FIG. 9D is a perspective view of a portion of the webbing shown in FIGS. 9A and 9B.

Best shown in FIG. 9D, the reinforcement cables 60 typically comprise multi-strand, high tensile strength cables 60, as these have been found to be highly resistant to cutting.

The restraints 10, 50 and strap 11 herein disclosed have been tested according to the parameters defined in Australian Standard AS 3555.1, 2003 Building Elements, Testing and Rating for Intruder Resistance. This has involved attempting to cut or otherwise destroy the restraints 10, 50 and strap 11 with a range of manually operated equipment up to 1 metre in length, such as bolt cutter, knives, shears, and the like. It has been found the restraints 10, 50, and specifically the strap 11, survive the destructive testing prescribed in this standard for an equivalent period or longer than a pair of conventional metal handcuffs. Thus, the terms, "substantially cut-resistant" or "cut-resistant" wherever used have been used in this context.

It will be apparent that obvious variations or modifications may be made which are in accordance with the spirit of the invention and which are intended to be part of the invention, and any such obvious variations or modifications are therefore within the scope of the invention.

In this specification, unless the context clearly indicates otherwise, the term "comprising" has the non-exclusive meaning of the word, in the sense of "including at least" rather than the exclusive meaning in the sense of "consisting only of". The same applies with corresponding grammatical changes to other forms of the word such as "comprise", "comprises" and so on.

INDUSTRIAL APPLICABILITY

The invention can be utilised in law enforcement, corrective services, immigration services, healthcare and the military.

The invention claimed is:

1. A restraint for non-injurious securement of a limb of a person to an object, the restraint comprising:
   a flexible strap defined by opposed ends and opposed edges and comprising, between the opposed ends, a substantially cut-resistant webbing enclosing a mesh strip comprised of interlinked rings; and
   at least one locking mechanism including a pivotable jaw portion being reversibly pivotable about an axis to a defined position, and one or more projections or pins that are adapted to be movable through the substantially cut-resistant webbing and into engagement with the interlinked rings and to disengage therefrom responsive to operation with a key received by a key receiver;
   wherein:
   the pivotable jaw portion is adapted to, upon pivoting to the defined position, operate the locking mechanism to move the one or more projections or pins;
   the flexible strap, when flexed into a loop, is able to be fixed into a fixed length loop by operating the locking mechanism to move the one or more projections or pins to extend through the substantially cut-resistant webbing and engage the interlinked rings; and
   the flexible strap is adapted to be able to be secured to the object with the fixed length loop adjusted to be able to encircle the limb of the person; and wherein the substantially cut-resistant webbing further encloses at least one reinforcement cable extending at least partially between the opposed ends of the flexible strap, in addition to the mesh strip comprised of interlinked rings; and wherein the at least one reinforcement cable is a pair of reinforcement cables; and the pair of reinforcement cables are arranged on opposing sides of the mesh strip comprised of interlinked rings; and wherein the substantially cut-resistant webbing is shaped into three tubular portions extending between the opposed ends of the flexible strap; and the mesh strip comprised of interlinked rings and the pair of reinforcement cables are each arranged to be enclosed within a separate one of the three tubular portions.

2. The restraint according to claim 1, wherein the at least one locking mechanism is configured to self-lock responsive to the one or more projections or pins moving beyond a defined threshold position.

3. The restraint according to claim 1, wherein the at least one locking mechanism comprises a slot dimensioned to receive the flexible strap, and the one or more projections or pins are arranged to move across and pass through the slot to engage with the mesh strip comprised of interlinked rings enclosed within the substantially cut-resistant webbing of the flexible strap.

4. The restraint according to claim 3, wherein the slot defines a direction along which a portion of the flexible strap is passed;

each of the one or more projections or pins have a free end arranged to abut the portion of the flexible strap in the slot;

and at least some of the free ends of the one or more projections or pins are curved in a direction perpendicular to the direction of the slot.

\* \* \* \* \*